(12) United States Patent
Wang et al.

(10) Patent No.: US 10,702,253 B2
(45) Date of Patent: Jul. 7, 2020

(54) NATURAL ORIFICE TRANSLUMENAL MINIMALLY INVASIVE SURGICAL APPARATUS

(71) Applicant: TIANJIN UNIVERSITY, Tianjin (CN)

(72) Inventors: Shuxin Wang, Tianjin (CN); Guokai Zhang, Tianjin (CN); Junbo Wei, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 176 days.

(21) Appl. No.: 15/765,929

(22) PCT Filed: Jun. 9, 2017

(86) PCT No.: PCT/CN2017/087729
§ 371 (c)(1),
(2) Date: Apr. 4, 2018

(87) PCT Pub. No.: WO2018/040662
PCT Pub. Date: Mar. 8, 2018

(65) Prior Publication Data
US 2018/0280010 A1    Oct. 4, 2018

(30) Foreign Application Priority Data

Aug. 27, 2016    (CN) .......................... 2016 1 0751855

(51) Int. Cl.
*A61B 17/00*    (2006.01)
*A61B 17/34*    (2006.01)
(Continued)

(52) U.S. Cl.
CPC .... *A61B 17/00234* (2013.01); *A61B 17/3421* (2013.01); *F16H 19/06* (2013.01);
(Continued)

(58) Field of Classification Search
CPC .......... A61B 17/00234; A61B 17/3421; A61B 1/00133; A61B 1/0051; A61B 1/00128;
(Continued)

(56) References Cited

U.S. PATENT DOCUMENTS

| | | | |
|---|---|---|---|
| 5,860,995 A | 1/1999 | Berkelaar | |
| 6,352,503 B1 * | 3/2002 | Matsui | ............... A61B 1/00071 600/104 |

(Continued)

FOREIGN PATENT DOCUMENTS

| | | |
|---|---|---|
| CN | 101637402 | 2/2010 |
| CN | 102309363 | 1/2012 |

(Continued)

OTHER PUBLICATIONS

Internaitonal Search Report and Written Opinion, issued in the corresponding PCT application No. PCT/CN2017/087729, dated Sep. 20, 2017, 14 pages.

(Continued)

*Primary Examiner* — Thomas C Diaz
(74) *Attorney, Agent, or Firm* — Hamre, Schumann, Mueller & Larson, P.C.

(57) ABSTRACT

Disclosed is a natural orifice translumenal minimally invasive surgical apparatus comprising a control box assembly sequentially connected with a hose assembly, a serpentine structure and a tip assembly at a middle position at a distal end of the control box assembly. Axes of the hose assembly and the serpentine structure are coincident with an axis of the tip assembly. The control box assembly is configured to position and replace a minimally invasive surgical instrument, support the surgical tool when being operated, and perform a minimally invasive surgery. The hose assembly is configured to provide passageways for the minimally invasive surgical instrument and a transmission wire and to (Continued)

output motions and loads. The tip assembly is configured to support the minimally invasive surgical instrument when being operated and enable the surgical instrument to have an enlarged motion space range. The apparatus has advantages including convenient operation, accurate actions and good real-time performance, achieves the basic goal of minimally invasive surgery, expands the flexibility of the movement, increases the operating space of the surgical instruments, and enables the minimally invasive surgery to be carried out in a handheld manner.

7 Claims, 6 Drawing Sheets

(51) Int. Cl.
*F16H 19/06* (2006.01)
*A61B 17/29* (2006.01)

(52) U.S. Cl.
CPC .................. *A61B 2017/003* (2013.01); *A61B 2017/00278* (2013.01); *A61B 2017/00318* (2013.01); *A61B 2017/00398* (2013.01); *A61B 2017/00477* (2013.01); *A61B 2017/00818* (2013.01); *A61B 2017/00876* (2013.01); *A61B 2017/00991* (2013.01); *A61B 2017/2906* (2013.01); *A61B 2017/3445* (2013.01); *A61B 2217/007* (2013.01)

(58) Field of Classification Search
CPC .......... A61B 1/018; A61B 2017/00318; A61B 2017/00398; A61B 2017/00477; A61B 2017/00818; A61B 2017/00876
See application file for complete search history.

(56) References Cited

U.S. PATENT DOCUMENTS

| | | | |
|---|---|---|---|
| 8,518,024 B2 * | 8/2013 | Williams | A61B 1/00052 606/1 |
| 2008/0188868 A1 | 8/2008 | Weitzner | |
| 2008/0269557 A1 | 10/2008 | Marescaux | |
| 2010/0286478 A1 * | 11/2010 | Ewers | A61B 1/00133 600/114 |
| 2011/0130787 A1 | 6/2011 | Cinquin et al. | |
| 2011/0230723 A1 | 9/2011 | Castro | |
| 2014/0373652 A1 | 12/2014 | Zergiebel | |
| 2015/0320437 A1 | 11/2015 | Worrell | |

FOREIGN PATENT DOCUMENTS

| | | |
|---|---|---|
| CN | 103110455 | 5/2013 |
| CN | 105796138 | 7/2016 |
| CN | 106264626 | 1/2017 |
| CN | 106361383 | 2/2017 |
| JP | 08224248 | 9/1996 |

OTHER PUBLICATIONS

Extended European Search Report for European patent application No. 17844969 dated Mar. 21, 2019.

* cited by examiner

NATURAL ORIFICE TRANSLUMENAL MINIMALLY INVASIVE SURGICAL APPARATUS

CROSS-REFERENCE TO RELATED APPLICATION

This application claims the benefit of Chinese Patent Application No. CN201610751855.7 filed on Aug. 27, 2016 in the State Intellectual Property Office of China, the whole disclosure of which is incorporated herein by reference.

BACKGROUND

Field of the Disclosure

The disclosure relates to a minimally invasive surgical apparatus, and more particularly to a natural orifice translumenal minimally invasive surgical apparatus.

Description of the Related Art

A natural orifice translumenal minimally invasive surgery does not leave any incision in a human body surface during treating a patient's disease, thereby mitigating a surgical trauma and postoperative pain and increasing a cosmetic result, thus achieving better physiological and psychological minimally invasive effects. For those persons who are obese, have poor health and scar constitution, and pursue better cosmetic results, this natural orifice translumenal minimally invasive surgery will be their best choice. However, surgical instruments are lack of flexibility and the surgical images are two-dimensional images, which increases difficulty of a surgical operation. As a result, a natural orifice translumenal surgical apparatus capable of increasing the flexibility of the surgical instruments and providing three-dimensional surgical images is proposed. During minimally invasive surgery, a surgeon performs surgical procedures by means of a slender minimally invasive surgical instrument. One end of the surgical instrument is operated by the surgeon, so that the other end of the surgical instrument is inserted into a human body through a natural orifice thereof for a surgical operation. Therefore, the surgical instrument is the only part in contact with a diseased tissue of the human body and the only tool for directly performing the surgical operation. During performing the surgery, since there is a special mapping relationship between movement of a distal end of the surgical instrument away from the surgeon and movement of a proximal end thereof handled by the surgeon, in order to satisfy operational requirements of different surgical operations (clamping, suturing, knotting, etc.), the surgeon must hold the surgical instrument to be moved in a large range, which may reduce flexibility of the distal end of the surgical instrument when performing surgical actions. Further, the long period and wide range operation will make the surgeon prone to fatigue, virtually increasing the difficulty of the surgical operation.

SUMMARY

The disclosure provides a natural orifice translumenal minimally invasive surgical apparatus, characterized in comprising a control box assembly, a hose assembly, a serpentine structure, and a tip assembly. The control box assembly is sequentially and fixedly connected with the hose assembly, the serpentine structure and the tip assembly at a middle position of a distal end thereof. The control box assembly comprises a control box housing having a rear wall provided with a quick-change device at either side thereof, the quick-change device including an upper connection sleeve into which a surgical tool is inserted, and a triangular drive assembly including a knob cap operable to move the tip assembly at the distal end. The hose assembly comprises an outer fixing sheath having a front end connected with an outer shell in which the serpentine structure is mounted.

Further, the triangular drive assembly comprises a toggle lever passing through a middle portion of an upper housing of the control box assembly. The toggle lever is connected with the knob cap by a key at a top portion thereof, rotatably connected onto a holder by a connection pin at a rear end of a bottom portion thereof, and rotatably connected with a rear end of a pull rod by a connection pin at a front end of the bottom portion thereof, the pull rod being rotatably connected with a slider by a pin at a front end thereof. The slider is slidably connected with the holder by a guide rail and slider structure, the holder is fixed onto a partition plate of the control box assembly, a spring is fixed to a front end of the slider at a rear end thereof and is fixed on a front wall of the holder at a front end thereof, and the slider has a sliding axis coincident with an axis of a guide rail of the holder. The apparatus further comprises a linear transmission wire having one end fixedly connected to one end of a triangular wire joint and the other end sequentially passing through a distal sheath assembly of the control box assembly, the hose assembly and the serpentine structure and then connected to a rear end of a transmission wire of the tip assembly.

Furthermore, the control box assembly further comprises two rotary switches. Each of the rotary switches comprises a swinging rod, at a top of which a swinging wheel is fixed, and a threaded bracket formed with a center hole in a top wall thereof and a cavity communicating with the center hole in a middle portion thereof. The swinging rod has a lower portion passing through the center hole of the threaded bracket and extending into the cavity, and is engaged with the center hole of the threaded bracket through a clearance fit. An externally-toothed gear is fixed to a bottom portion of the swinging rod located in the threaded bracket, and an upper magnet assembly is fixed to a bottom wall of the externally-toothed gear.

Moreover, the threaded bracket is fixed to a threaded seat, which is fixed onto a fixing plate by a fixing bolt. An internally-geared ring is fixed in the threaded bracket. A lower magnet assembly is fixed in an inner wall of a bottom portion of the threaded seat at a position opposite to the upper magnet assembly. The externally-toothed gear is supported on a thrust spring. The upper magnet assembly is wrapped within the thrust spring. The thrust spring has an upper end in contact with a lower end of the externally-toothed gear in a non-stressed state thereof and a lower end fixedly connected with the lower magnet assembly. A packing washer is sleeved over the thrust spring located at a lower portion of the internally-geared ring to radially fix the thrust spring. Axes of the internally-geared ring and the externally-toothed gear are coincident with an axis of the swinging rod, and the swinging rod is movable in an up-and-down direction to cause the internally-geared ring to engage with or disengage from the externally-toothed gear. Sprockets are mounted on the swinging rod located at an upper part of the threaded bracket.

Furthermore, a set of chutes are fixed to the partition plate at a front side of each of the sprocket, respectively. Each set of chutes comprises two chutes disposed at a predetermined interval, and the sprocket on each swinging rod is engaged with a chain surrounding the sprocket. Each of the chains has two free ends disposed within the two chutes of one set of the chutes, respectively, and the chain is drivable by the swinging rod to reciprocate linearly in the chute. Both of the free ends of each chain are connected with one end of four transmission wire, and the other end of each of the four transmission wires sequentially passes through the distal sheath assembly, a guide wire hole of a connection ring of the hose assembly and a guide wire hole of the serpentine structure and is then fixed in an rear end opening of a tip body of the tip assembly.

In addition, the two quick-change devices comprise two lower connection sleeves fixedly connected on the left and right sides of a rear wall of a lower housing of the control box housing, respectively. Each of the lower connection sleeves has a front end fixedly connected with a rear end of the tool tube at a corresponding side. Each of the lower connection sleeves is sleeved with and fixed to an outer telescopic sleeve having a center hole into which a middle telescopic sleeve is slidably inserted, and the middle telescopic sleeve has a center hole into which an inner telescopic sleeve is slidably inserted. An upper connection sleeve is fixed to a rear end of the inner telescopic sleeve and is symmetrically formed with two rectangular slots of the same structure at either side along an axis thereof, and two unlocking bars of the same structure each comprise a straight bar segment inserted into the rectangular slot at a corresponding side through a clearance fit. The straight bar segment has a rear end provided with a protruding hook hooked with a groove in the surgical tool and a front end connected with a pressing plate, and the bar segment of each unlocking bar is rotatably connected with the upper connection sleeve by a rotation shaft. The upper connection sleeve has a portion opposite to the pressing plate and fixedly connected with a push rod by a spring, wherein the pressing plate is allowed to be in contact with a top portion of the push rod when the unlocking bar is rotated about the rotation shaft.

Further, the tip assembly comprises a tip body and an opening-closing body mounted in a middle groove of the tip body. The opening-closing body includes two triangular rings having the same structure and symmetrically arranged in a left-and-right direction, and a triangular pulling rod is disposed at a middle position between the two triangular rings. Each of the triangular rings is symmetrically provided with a cylindrical boss and a cylindrical hole at either side thereof, wherein the cylindrical boss has an axis parallel to an axis of the cylindrical hole and perpendicular to an axis of the triangular ring, and each of the cylindrical bosses is rotatably connected with one end of each of links comprising two front links and two rear links, and the other ends of the two front links and the two rear links are respectively rotatably connected to front and the rear ends of the triangular pulling rod by pins. A front end of a stretching wire is vertically and fixedly connected onto the triangular pulling rod, a triangular spring is sleeved over the stretching wire, and a rear end of the stretching wire passes through a middle opening of the tip body in which a boss is arranged. The triangle spring is disposed in the middle opening with a predetermined gap therebetween and is fixedly connected to the boss at a lower end thereof, wherein in a state where axes of the two triangular rings are parallel with each other, an upper end of the triangular spring is in contact with a bottom end of the triangular pulling rod, and each cylindrical hole is rotatably connected with a cylindrical side of a triangular pin fixed onto the tip body, so that the triangular ring is rotatable about the triangular pin. The tip body is provided with arc grooves in a middle slotted inner wall thereof corresponding to the four cylindrical bosses, and an end portion of each cylindrical boss of the triangular rings is slidably disposed in a corresponding one of the arc grooves, the cylindrical boss is slidable back and forth in the arc groove, and the triangular pulling rod, the links, the triangular pin and the triangular ring are rotatably connected together to form a four-link mechanism.

In addition, the natural orifice translumenal minimally invasive surgical apparatus further comprises a water-air switch connected onto the upper housing.

The present disclosure at least provides follow advantageous effects: the disclosure provides a manual operation device based on wire transmission, which employs wire transmission technology, and thus has small overall structure in volume and is convenient in operation. The deformable hose assembly and the openable tip assembly are adopted to passively realize the surgical operation of the surgical instrument and expand the surgical flexibility of the surgical instrument, thereby facilitating the surgical operation by the surgeon. When completing a surgical operation, the knob switch is operated to lock and unlock the surgical instrument and set the body position of the minimally invasive surgery according to the desired action of the surgeon, thereby facilitating the smooth progress of minimally invasive surgery with safe and efficient and strong operability. Further, there are two functions including providing exchangeable surgical instruments and rapid exchanging instrument tools. Thus, flexible actions in minimally invasive surgery can be effectively achieved to meet the requirements of different surgical operation tasks.

BRIEF DESCRIPTION OF THE DRAWINGS

In order to make objects, technical solutions and beneficial effects of the present disclosure clearer, the disclosure provides the following drawings for illustration.

DETAILED DESCRIPTION OF PREFERRED EMBODIMENTS

Figure 1:
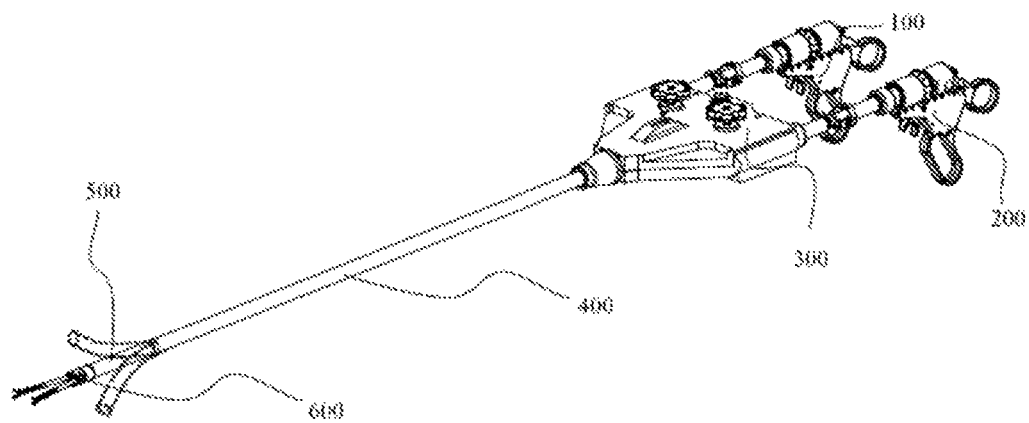
FIG. 1 is a schematic structural view of an overall structure of a natural orifice translumenal minimally invasive surgical apparatus according to an embodiment of the disclosure.

The preferred embodiments of the disclosure will be described in further detail below, by way of example, with reference to the accompanying drawings.

It should be noted that directional terms such as "upper", "lower", "front", "rear", "left", "right", "proximal", "distal" and the like mentioned in the disclosure only refer to directions described with reference to the accompanying drawings, rather than limiting the scope of the disclosure. The same elements are denoted by the same or similar reference numerals throughout the drawings. Conventional structures or constructions may be omitted as they may cause confusion about the understanding to the disclosure. In addition, a shape and a size of each component in the drawings do not reflect the true size and scale thereof, and merely illustrate the content of the embodiments of the disclosure.

FIG. 1 is a schematic structural view of an overall structure of a natural orifice translumenal minimally invasive surgical apparatus according to an embodiment of the disclosure. The natural orifice translumenal minimally invasive surgical apparatus comprises a control box assembly 300, a hose assembly 400 fixedly connected at a middle position at a distal or front end of the control box assembly 300, and a serpentine structure 500 and a tip assembly 600 provided within the hose assembly 400. Axes of the hose assembly 400, the serpentine structure 500 and the tip assembly 600 coincide with each other. The control box assembly 300 is connected with left and right surgical tools 100, 200 at a proximal or rear end thereof.

Figure 2A:
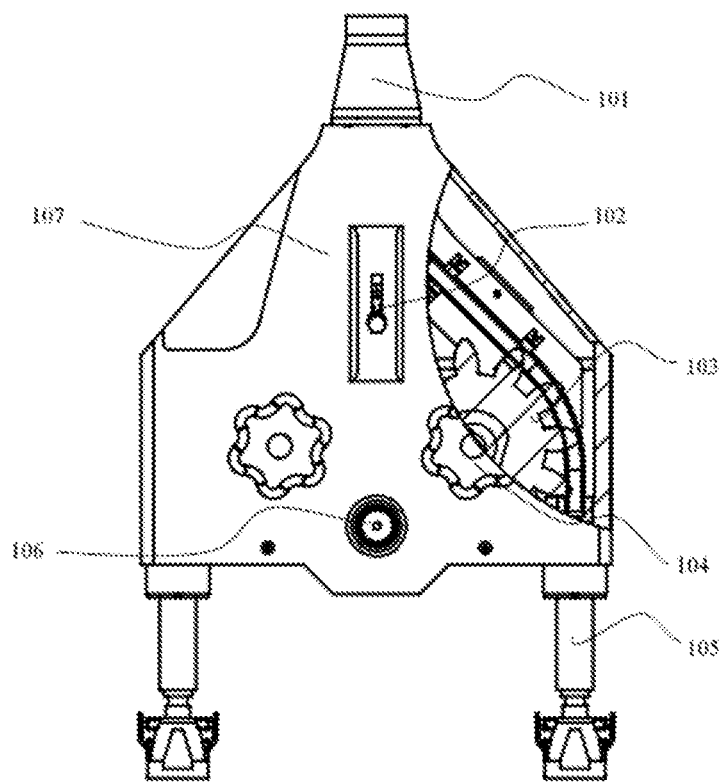
FIG. 2A is a schematic structural view of an overall structure of a control box assembly of a natural orifice translumenal minimally invasive surgical apparatus according to an embodiment of the disclosure.
Figure 2B:
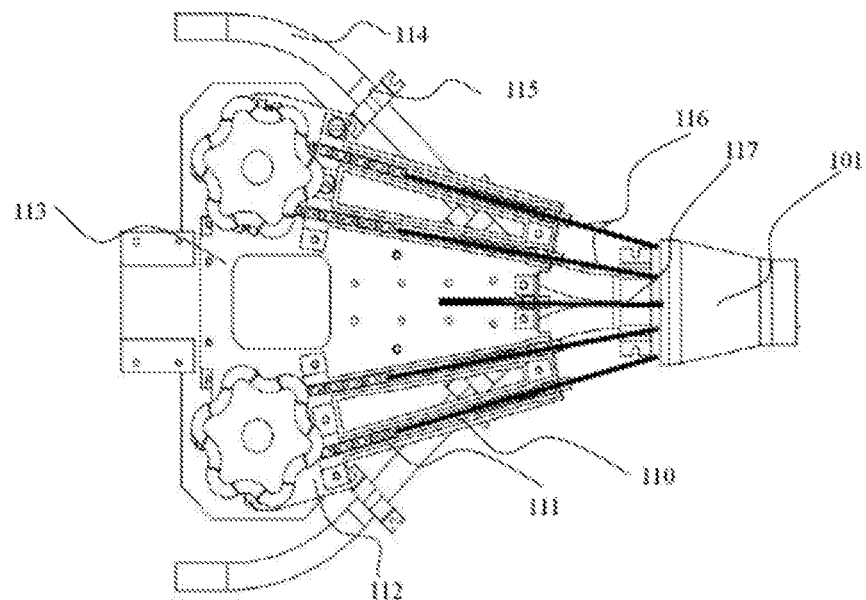
FIG. 2B is a schematic structural view of an internal structure of the control box assembly shown in FIG. 2A.
Figure 2C:
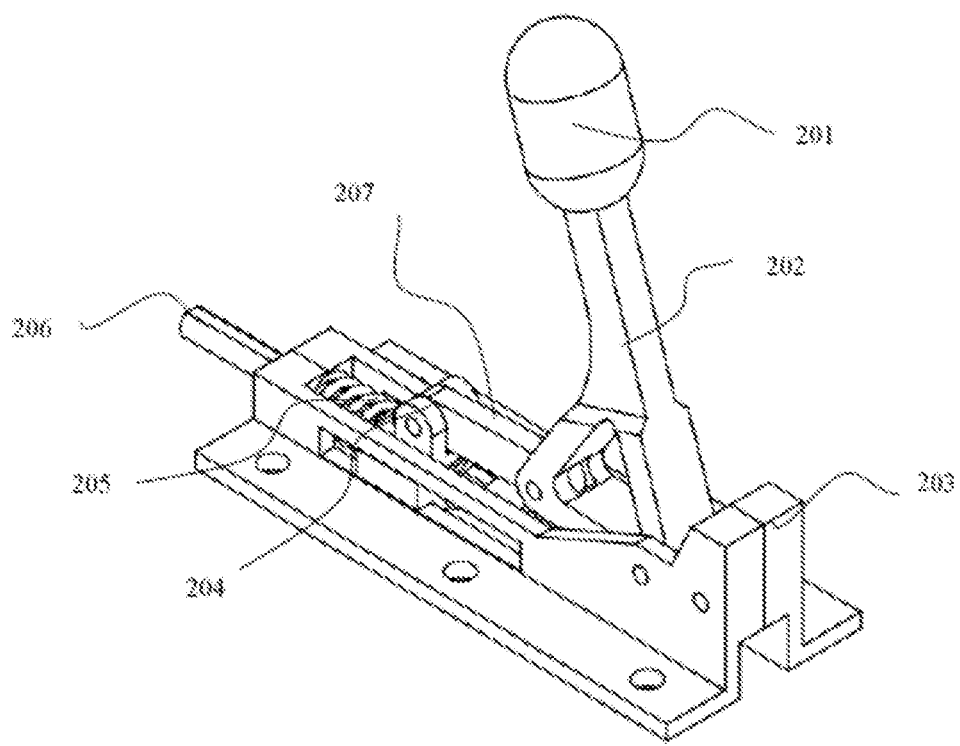
FIG. 2C is a schematic view of a triangular driving assembly of the control box assembly shown in FIG. 2A.

Referring to FIGS. 2A and 2B, the control box assembly 300 is a manipulation assembly of the natural orifice translumenal minimally invasive surgical apparatus. In some embodiments, the control box assembly 300 may comprise a front sheath assembly 101 having a rear end fixedly connected with a front end of a control box housing 107. The front sheath assembly 101 provides passages for the surgical tools 100 and 200 and for a drive wire for control action of the control box assembly 300. Therefore, the front sheath assembly 101 has a predetermined rigidity, and thus plays an important connecting role. The front sheath assembly 101 has a front end sequentially connected with the serpentine structure 500 and the tip assembly 600 by the hose assembly 400. Specifically, the control box housing 107 may include a lower housing and an upper housing fixed onto the lower housing. A fixing plate 113 is fixed to the lower housing by a pin. Two tool tubes 114 with the same structure are fixed onto the fixing plate 113 by a pressing block 115 and arranged symmetrically in a left-and-right direction. A front end of each of the tool tubes 114 is disposed within the front sheath assembly 101 at thereof. The tool tube 114 serves as a passage for the surgical tool. Partition plates 112 may be fixed on the fixing plate 113 by a pin, and chutes 110 may be fixedly connected to the partition plate 112 by a pin, respectively.

Referring to FIG. 2A, the control box assembly 300 may further comprise a triangular drive assembly 102 connected between the partition plates 112. The triangular drive assembly 102 includes a knob cap 201 operable by a surgeon to achieve movement of the tip assembly 600.

In some embodiments, the triangular drive assembly 102 may comprise a toggle lever 202 passing through a middle portion of the upper housing. The knob cap 201 is connected to a top portion of the toggle lever 202 by a key. The knob cap 201 can serve as a manually operated object for pulling the toggle lever 202 back and forth. The toggle lever 202 is rotatably connected onto a holder 203 by a connection pin at a rear end of a bottom thereof so as to rotate about the connection pin. Further, the toggle lever 202 is rotatably connected with a rear end of a pull rod 207 by a connection pin at a front end of the bottom thereof. The pull rod 207 is rotatably connected with a slider 204 by a pin at a front end thereof. The slider 204 is slidably connected with the holder 203 by a guide rail and slider structure, thereby rotation of the toggle lever 202 can be converted into a linear movement of the slider 204. The holder 203 is fixed onto the partition plate 112. A spring 205 is fixed to a front end of the slider 204 at a rear end thereof and is fixed on a front wall of the holder 203 at a front end thereof. The slider 204 has a sliding axis coincident with an axis of a guide rail of the holder 203. A linear transmission wire 117 has one end fixedly connected to one end of a triangular wire joint 206 and the other end sequentially passing through the front sheath assembly 101, a guide wire hole in a connection ring 702 of the hose assembly 400 and the serpentine structure 500 and then connected to a rear end of a stretching wire 609 of the tip assembly 600.

With the above configuration, the spring 205 is normally extended such that the slider 204 is close to the toggle lever 202, and the slider 204 is normally kept away from a front wall of the holder 203. The spring 205 may be compressed by pressing the toggle lever 202 downwardly. When being released, the toggle lever 202 is returned to an original position by an elastic force of the spring 205. The holder 203 is formed with a cylindrical hole in the front wall thereof. A rear end of the triangular wire joint 206 passes through the cylindrical hole and the spring 205 and is fixedly connected with the slider 204. The triangular wire joint 206 has an axis coincident with the sliding axis of the slider 204. Manually pulling the toggle lever 202 will drive the pull rod 207 to be moved. Since the pull rod 207 is connected to one end of the slider 204, the linear movement of the slider 204 will drive the triangular wire joint 206 to be moved.

Figure 2D:
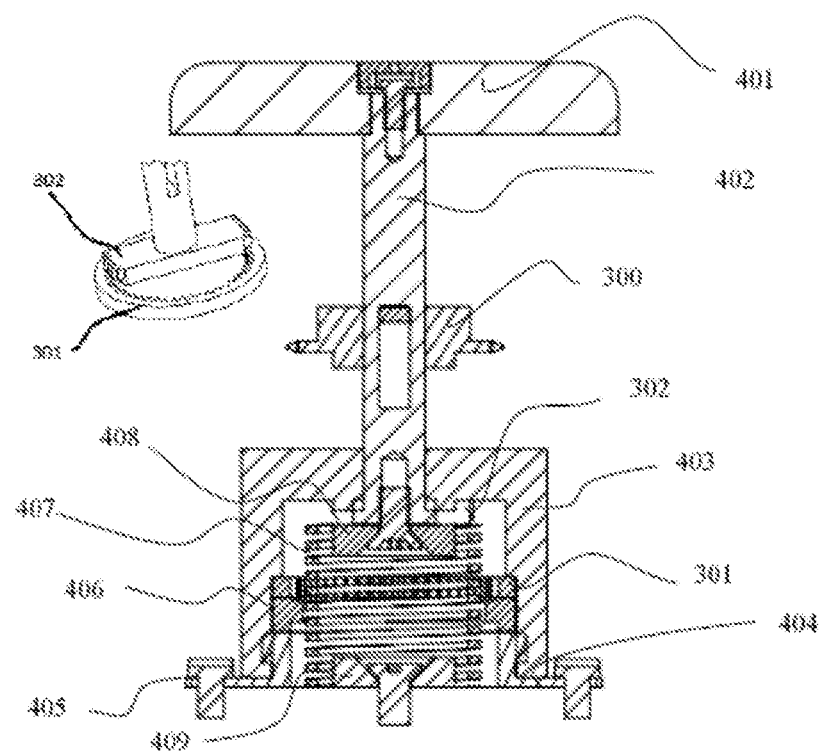
FIG. 2D is a schematic structural view of a rotary switch of the control box assembly shown in FIG. 2A.

Referring to FIGS. 2A and 2D, in some embodiments, the control box assembly 300 further comprises two rotary switches 104 disposed symmetrically in the left-and-right direction on a rear side of the partition plate 112 respectively and serving as transmission components of the minimally invasive surgery control box. The two rotary switches 104 have the same structure. Each rotary switch 104 includes a swinging rod 402, at a top of which a swinging wheel 401 is fixed, and a threaded bracket 403 formed with a center hole in a top wall thereof and a cavity communicating with the center hole in a middle portion thereof. The swinging rod 402 has a lower portion passing through the center hole of the threaded bracket 403 and extending into the cavity. The swinging rod 402 is engaged with the center hole of the threaded bracket 403 through a clearance fit. An externally-toothed gear 302 is fixed to a bottom portion of the swinging rod 402 located in the threaded bracket 403. An upper magnet assembly 408 is fixed to a bottom wall of the external gear 302. The threaded bracket 403 is fixed to a threaded seat 404 fixed onto the fixing plate 113 by a fixing bolt 405. An internally-geared ring 301 is fixed in the threaded bracket 403. A lower magnet assembly 409 is fixed to an inner wall of a bottom portion of the threaded seat 404 opposite to the upper magnet assembly 408. The externally-toothed gear 302 is supported on a thrust spring 407. The upper magnet assembly 408 is wrapped within the thrust spring 407. An upper end of the thrust spring 407 is in contact with a lower end of the externally-toothed gear 302 in a normal state, i.e., in a non-stressed state. The thrust spring 407 is fixedly connected with the lower magnet assembly 409 at a lower end thereof. A packing washer 406 is sleeved or fitted over the thrust spring 407 located at a lower portion of the internally-geared ring 301 to radially fix the thrust spring 407, thereby functioning as a limiting device. Axes of the internally-geared ring 301 and the externally-toothed gear 302 are coincident with the axis of the swinging rod 402. The swinging rod 402 is movable in an up-and-down direction to cause the internally-geared ring 301 to engage with or disengage from the externally-toothed gear 302. Sprockets 103 are mounted on the swinging rod 402 located at an upper part of the threaded bracket. The sprockets 103 include left and right sprockets 103 having the same structure.

According to the above configuration, the thrust spring 407 is extended in the normal state, i.e., in the non-stressed state. The externally-toothed gear 302 is brought close to an upper end surface of an inner wall of the threaded bracket 403 by the extending force of the spring, so that the externally-toothed gear 302 is not engaged with the internally-geared ring 301. By manually rotating the swinging wheel 401, the swinging rod 402 is driven to be rotated so as to drive the externally-toothed gear 302 to be rotated. By manually pushing the swinging wheel 401 downwardly, the externally-toothed gear 302 and the upper magnet assembly 408 move downwardly together with the swinging wheel 401. The downward movement of the externally-toothed gear 302 presses the thrust spring 407 such that the thrust spring 407 is in a compressed state. When a distance between the upper magnet assembly 408 and the lower magnet assembly 409 becomes smaller, the upper magnet assembly 408 is attracted to the lower magnet assembly 409. At this time, the externally-toothed gear 302 and the internally-geared ring 301 are located in a same plane and thus engaged with each other, and friction contact of the internally-geared ring 301 with the externally-toothed gear 302 prevents the swing wheel from being rotated, thereby locking the control box assembly. The threaded bracket 403 can fix the swinging rod 402 to some extent in an axial direction. If the swinging wheel 401 is manually pulled upwardly, the distance between the upper magnet assembly 408 and the lower magnet assembly 409 becomes larger and an attractive force between the magnet assemblies become smaller than the extending force of the thrust spring 407. Thus, the externally-toothed gear 302 is moved upwardly to be disengaged from the internally-geared ring 301 under the extending force of the thrust spring 407, thereby unlocking the surgical control box assembly. The swinging rod 402 then continues to move upwardly to restore to its initial state, and the externally-toothed gear 302 is in contact with the upper end of the thread bracket 403, thereby realizing a non-linear action switch.

Referring to FIG. 2B, when the rotary switch 104 is operated to be moved upwardly so that the internally-geared ring 301 is disengaged from the externally-toothed gear 302, the surgical control box is unlocked. The swinging rod 402 is rotatable about its own axis, and the sprockets 103 key-fitted with the swinging rod 402 is rotated with rotation of the swinging rod 402. A set of chutes 110 are fixed to the partition plates 112 at a front side of each sprocket 103, respectively. Each set of chutes 110 includes two chutes 110 disposed at a predetermined interval. The sprocket 103 on each swinging rod 402 is engaged with a chain 111 surrounding the sprocket 103. Each of the chains 111 has two free ends disposed within the two chutes 110 of one set of the chutes 110, respectively. The chain 111 is driven by the swinging rod 402 to reciprocate linearly in the chutes 110. Both of the free ends of each of the chains 111 are connected with one end of each of four transmission wires 116, and the other end of each of the four transmission wires 116 sequentially passes through the front sheath assembly 101, the guide wire hole of the connection ring 702 and a guide wire hole of the serpentine structure 500, and is then fixed in an rear end opening of a tip body 607 of the tip assembly 600. The transmission wire 116 is slidable back and forth in the guide wire hole of the connection ring 702 so as to be tensioned and relaxed, so that the serpentine structure 500 is moved in a bended way by the pulling action of the transmission wire to achieve actions of the distal hose assembly 400, thereby allowing operating the front end of surgical apparatus to pitch and swing. The transmission wires 116 may be connected with the serpentine structure 500 by a known connection structure, and the transmission wire 116 may be slidable in the guide wire hole. The rotary switch 104 is manually operated to be rotated about its own axis so as to drive the sprockets 103 to be rotated together therewith, so that the chains 111 fixedly connected onto the sprockets 103 are moved linearly. The linear movement of the chains 111 drives the transmission wire 116 to slide in the guide wire hole, and the linear movement of the transmission wires 116 drives the serpentine structure 500 of the surgical apparatus to be moved, thereby achieving a desired surgical passage structure. When the rotary switch 104 is pressed downwardly so that the internally-geared ring 301 is engaged with the externally-toothed gear 302, the rotary switch 104 can not be rotated, thereby locking the control box assembly. In this case, the transmission wire is kept in the tensioning state so that the distal surgical tool is in a position locking state. Referring to FIG. 1, the rotary switch 104 is manually operated to drive the transmission wires 116 to be tensioned and moved linearly, which allows the distal serpentine structure 500 to be bent upwardly or downwardly and to swing in the left-and-right direction, thereby adjusting the placement of the surgical apparatus. The locking of the up-and-down pitch and left-and-right swinging positions of the distal snake-bone structure 500 is realized by the engagement state of the two sets of gears. The realization of the up-and-down pitch and left-and-right swinging movement may refer to a wire connection structure disclosed in CN200910306053.5, thereby increasing the range of reachable surgical space of the surgical apparatus.

Figure 2E:
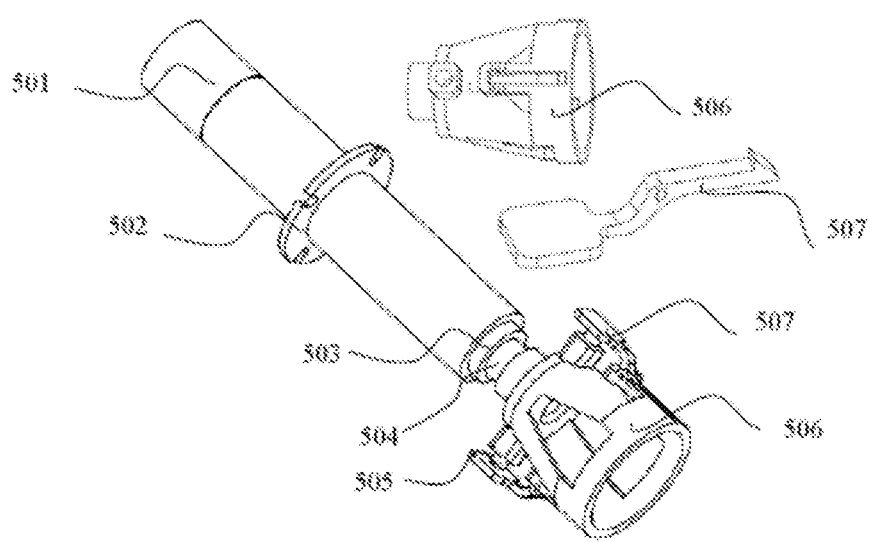
FIG. 2E is a schematic structural view of a quick-change device of the control box assembly shown in FIG. 2A.

Referring to FIGS. 2A and 2E, the control box housing 107 is provided with two quick-change devices 105, which are arranged, as important components for performing a minimally invasive surgery, at left and right sides of a rear wall of the lower housing of the control box housing 107, respectively. The two quick-change devices 105 include two lower connection sleeves 501 fixedly connected on the left and right sides of the rear wall of the lower housing of the control box housing 107, respectively. Each of the lower connection sleeves 501 has a front end fixedly connected with the rear end of the tool tube 114 at the corresponding side. Each of the lower connection sleeves 501 is sleeved and fixed with an outer telescopic sleeve 502 having a center hole into which a middle telescopic sleeve 503 is slidably inserted. The middle telescopic sleeve 503 has a center hole into which an inner telescopic sleeve 504 is slidably inserted. An upper connection sleeve 506 is fixed to a rear end of the inner telescopic sleeve 504. The upper connection sleeve 506 is symmetrically formed with two rectangular slots of the same structure at either side along an axis thereof. Two unlocking bars 507 of the same structure each comprise a straight bar segment inserted into the rectangular slot at the corresponding side through a clearance fit. The straight bar segment has a rear end provided with a protruding hook hooked with a groove in the surgical tool. Further, the straight bar segment has a front end connected with a pressing plate. The bar segment of each unlocking bar 507 is rotatably connected with the upper connection sleeve 506 by a rotation shaft. A portion of the upper connection sleeve 506 opposite to the pressing plate is fixedly connected with a push rod 505 by a spring. When the unlocking bar 507 is rotated about the rotation shaft, the pressing plate may contact with a top portion of the push rod 505.

When the surgical tool is inserted through the upper connection sleeve 506 of the quick-change device 105, passes through the middle hole of the inner telescopic sleeve 504 and is positioned within the quick-change device 105, the groove within the surgical tool is engaged with the hook of the unlocking bar 507 by frictionally pressing a front end of a bar end of the unlocking bar 507. The straight bar segment of the unlocking bar 507 at a front end thereof is pressed by a force against the pressing plate at a rear end of the unlocking bar 507 so as to be in contact with the push rod 505, so that the front end of the unlocking bar 507 is held in a fixed position, thereby securing the surgical tool. The pressing plate of the unlocking bar 507 is manually pressed to compress the spring sleeved or fitted over the push rod 505, thereby changing the cooperation relationship of the push rod 505 with the unlocking bar 507 of the quick-change device 105, so that the straight bar section of the unlocking bar 507 is deflected outwardly to disengage the hook on the front end of the unlocking bar 507 from the groove within the surgical tool, thereby disassembling the surgical tool for quickly replacing the surgical tool.

In some embodiments, an air-water switch 106 may be connected to the upper housing to facilitate the operation of the surgeon. The water-gas switch 106 is connected with a water pipe to access a water source. The water-vapor switch 106 may be turned on to clean a lens, so that the surgeon can perform the surgery with good visual field. Also, the water-vapor switch 106 may be turned on to clean organ surface of the human body. During performing the surgery, there may be bleeding. In this case, the air-water switch 106 is activated to clean the organs to be subject to the surgery, which may improve security of the surgical operation. The air-water switch 106 may have the existing structure in the prior art.

Figure 3A:
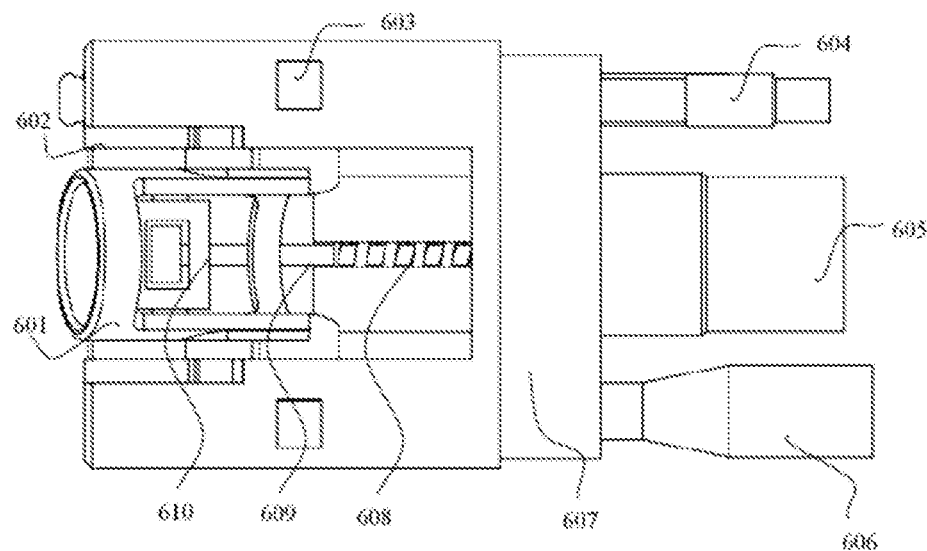
FIG. 3A is a schematic structural view of a tip assembly of a natural orifice translumenal minimally invasive surgical apparatus according to an embodiment of the disclosure.
Figure 3B:
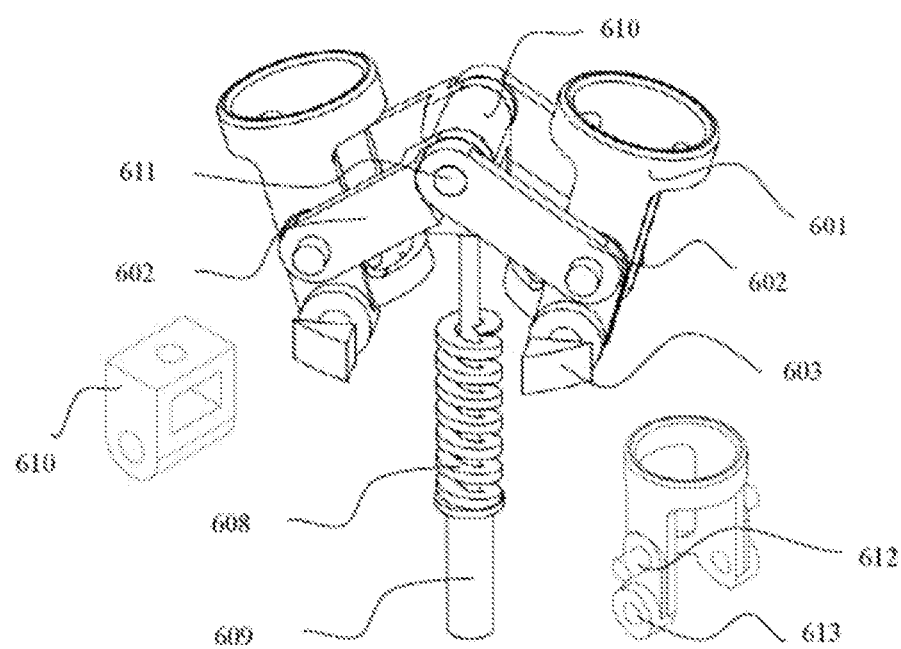
FIG. 3B is a schematic structural view of an opening and closing body of the tip assembly shown in FIG. 3A.
Figure 3C:
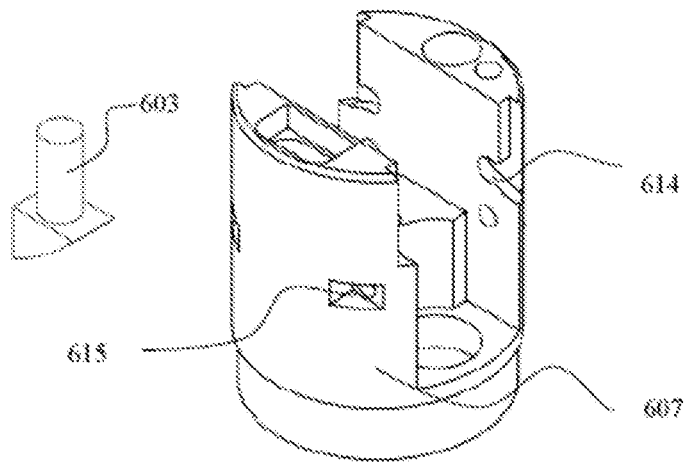
FIG. 3C is a schematic structural view of a tip body of the tip assembly shown in FIG. 3A.

Referring to FIGS. 3A and 3B, the tip assembly 600 provides a support passage for an end effector of the minimally invasive surgical instrument. The tip assembly 600 enables connecting the end effector of the surgical tool with the hose assembly 400 of the surgical apparatus. The tip assembly 600 comprises a tip body 607 and an opening-closing body mounted in a middle groove of the tip body 607. The opening-closing body includes two triangular rings 601 having the same structure and symmetrically arranged in the left-and-right direction. A triangular pulling rod 610 is disposed at a middle position between the two triangular rings 601. Each of the triangular rings 601 is symmetrically provided with a cylindrical boss 612 and a cylindrical hole 613 at either sides thereof. The cylindrical boss 612 has an axis parallel to an axis of the cylindrical hole 613 and perpendicular to the axis of the triangular ring 601. Each of the cylindrical bosses 612 is rotatably connected with one end of each of links 602 including two front links 602 at a front side of the triangular pulling rod 610 and two rear links 602 at a rear side of the triangular pulling rod. The other ends of the two front links 602 and the two rear links 602 are respectively rotatably connected to front and the rear ends of the triangular pulling rod 610 by pins 611. A front end of a stretching wire 609 is vertically and fixedly connected onto the triangular pulling rod 610. A triangular spring 608 is sleeved or fitted over the stretching wire 609. A rear end of the stretching wire 609 passes through a middle opening of the tip body 607 in which a boss is arranged. The triangle spring 608 is disposed in the middle opening with a predetermined gap therebetween and is fixedly connected to the boss at a lower end thereof. When axes of the two triangular rings 601 are parallel with each other, an upper end of the triangular spring 608 is in contact with a bottom end of the triangular pulling rod 610, and each cylindrical hole 613 is rotatably connected with a cylindrical side of a triangular pin 603 fixed onto the tip body 607, so that the triangular ring 601 is rotatable about the triangular pin 603. As an implementation of the embodiments of the present disclosure, the triangular pin 603 has a triangular prism structure. The tip body 607 is formed with a triangular prism hole 615 into which the triangular prism structure is fixed. The tip body 607 is provided with arc grooves 614 in a middle slotted inner wall thereof corresponding to the four cylindrical bosses 612. An end portion of each cylindrical boss 612 of the triangular rings 601 is slidably disposed in a corresponding one of the arc grooves 614. The cylindrical boss 612 is slidable back and forth in the arc groove 614. The triangular pulling rod 610, the links 602, the triangular pin 603 and the triangular ring 601 are rotatably connected together to form a four-link mechanism.

Figures 3D, 3E:
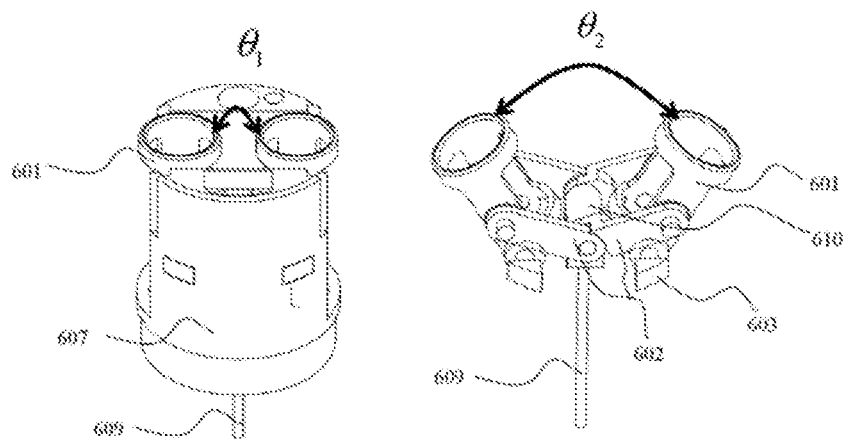
FIG. 3D is a schematic view of an initial attitude of the tip assembly shown in FIG. 3A.
FIG. 3E is a schematic view of the tip assembly shown in FIG. 3A, showing an enlarged triangular operation region.

The stretching wire 609 is pulled to move linearly downwards so as to drive the triangular pulling rod 610 to compress the triangular spring 608 to move downwards. The link 602 rotatably connected to the triangular pulling rod 610 is pulled to be rotated to drive the cylindrical boss 612 of the right triangular ring 601 to slide in the arc groove 614 in the tip body 607, so that the triangular ring 601 is correspondingly rotated outwardly about the triangular pin 603. Similarly, the rotation of the pulling rod 602 drives the left triangle ring 601 to be rotated outwardly, and thereby the two triangular rings 601 are respectively rotated outwardly so that a larger angle is formed between the two triangular rings 601, thereby realizing movement output of the triangular rings 601 of the distal tip assembly 600 of the natural orifice translumenal surgical apparatus. In an initial attitude shown in FIG. 3D, a small angle $\theta_1$ is formed between the left and right triangular rings 601. The triangular drive assembly 102 is manually operated and the stretching wire 609 is tensioned to reach an attitude shown in FIG. 3E in which a large angle $\theta_2$ is formed between the left and right triangular rings 601, thereby outputting different output angles to obtain desired surgical body position settings. The distal tip assembly is moved by rotating the knob cap 201 of the control box by the surgeon, thereby realizing an enlarged triangular surgical operation range of the surgical apparatus.

The two surgical tools 100, 200 sequentially pass through the connection sleeves 506 at the corresponding sides, the tool tubes 114 of the control box at the corresponding sides, the front sheath assembly 101 of the surgical apparatus, the tool hole of the connection ring 702 of the hose assembly 400 and the serpentine structure 500, respectively. The rear ends of the two surgical tools 100 and 200 are fixed through the engagement of the groove with the hook of the unlocking bar 507, respectively. The distal end effector of each surgical tool passes through a surgical tool passageway 605 and is disposed within the triangular ring 601 of the tip assembly 600 of the surgical apparatus at the corresponding side in a clearance fit manner, respectively. The end effector of each surgical tool is passively disposed in the triangular ring 601 to be moved together with the triangular ring 601 correspondingly.

Figure 4:
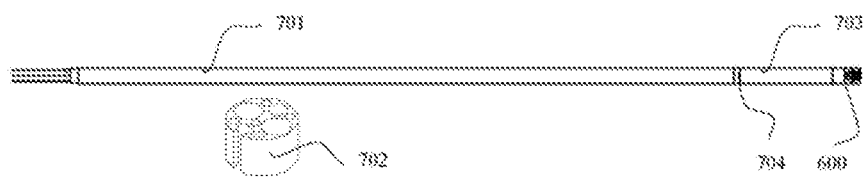
FIG. 4 is a schematic structural view of a hose assembly in a natural orifice translumenal minimally invasive surgical apparatus according to an embodiment of the disclosure.
Figure 5:
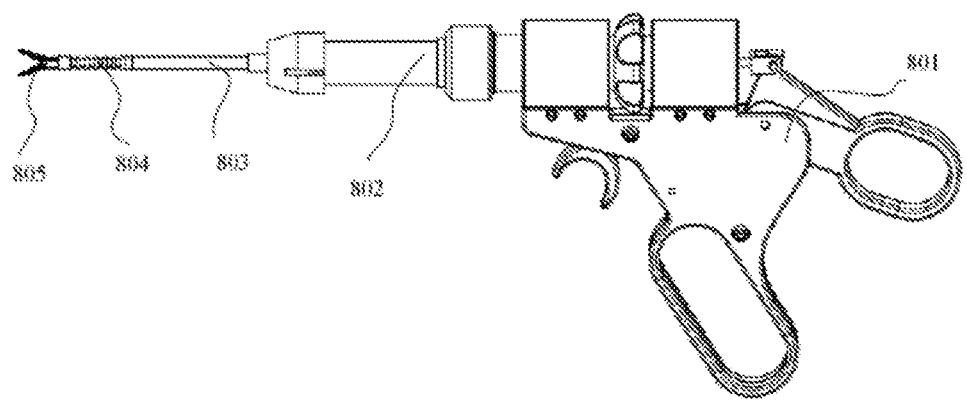
FIG. 5 is a schematic structural view of a surgical tool installed in a natural orifice translumenal minimally invasive surgical apparatus according to an embodiment of the disclosure.

Referring to FIG. 4, the hose assembly 400 provides a passageway for the minimally invasive surgical tool and the transmission wire. The hose assembly 400 is in direct contact with the natural orifice of the human body, thus has good softness without damage to the natural orifice of the human body. In some embodiments, the hose assembly 400 comprises an outer fixing sheath 701 fixedly connected with the front sheath assembly 101 to form a unitary structure therewith. As an implementation, the outer fixing sheath 701 is a rubber tube and is sequentially connected with the connection ring 704 and an outer shell 703 at a front end thereof. Four connection rings 702 are fixedly arranged within the out fixing sheath 701 at a predetermined interval in a front-and-back direction thereof. Each of the connection rings 702 is provided with a plurality of cylindrical guide wire holes and two tool holes. The surgical tools 100 and 200 pass through the tool hole of the hose assembly 400. The serpentine structure 500 is installed within the outer shell 703.

Figure 6:
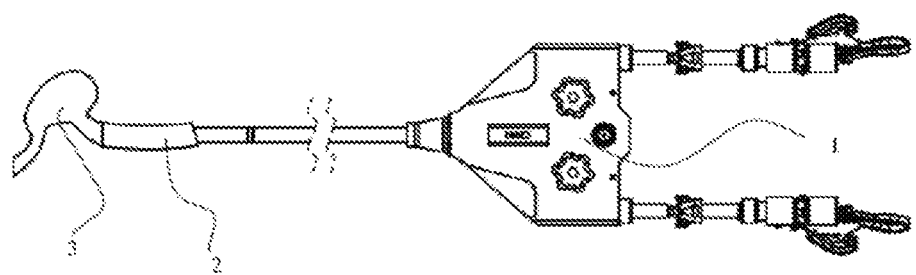
FIG. 6 is a schematic view of application of a natural orifice translumenal minimally invasive surgical apparatus according to an embodiment of the disclosure in a stomach surgical operation.

FIG. 6 is a schematic view of application of the natural orifice translumenal minimally invasive surgical apparatus according to an embodiment of the disclosure in a stomach surgical operation. The end effector of the surgical tool of the minimally invasive surgical apparatus 1 according to the embodiment of the disclosure illustrated in FIG. 6 is extended into a stomach 3 through an esophagus 2 of the human body to perform a surgical operation. The end effectors of the surgical tools 100, 200 are in direct contact with the stomach 3 of the human body. The hose assembly 400 of the surgical apparatus is in direct contact with the esophagus 2 of the human body.

In some embodiments, the natural orifice translumenal minimally invasive surgical apparatus is operated as follows.

With the natural orifice translumenal minimally invasive surgical apparatus, the minimally invasive surgical tool is held by the surgeon. The surgical apparatus is firstly placed properly by a surgeon. The control box assembly 300 is fixed in position. The different left and right rotary switches 104 are adjusted to control different actions, respectively. The left rotary switch 104 performs a pitch motion of the distal serpentine structure 500 of the surgical apparatus, and the right rotary switch 104 swings the serpentine structure 500 in the left-and-right direction. Referring to FIG. 1, the surgeon faces the control box assembly 300, which is normally in an unlocked state, rotates the left rotary switch 104 counterclockwise to pitch upwardly the distal serpentine structure 500, and presses the rotary switch 104 downwardly to lock the surgical control box assembly 300. At this time, the distal serpentine structure 500 of the surgical apparatus is maintained in an upward pitching state. If the rotary switch 104 is pulled upwardly, the control box assembly 300 is unlocked. When the left rotary switch 104 is rotated clockwise, the distal serpentine structure 500 is pitched downwardly. When the control box assembly 300 is in the unlocked state under the normal condition, the right rotary switch 104 is rotated counterclockwise to swing the distal snake-bone structure 500 leftwards. Then, the rotary switch 104 is depressed downwardly to lock the surgical control box assembly 300. At this time, the distal serpentine structure 500 of the surgical apparatus is maintained in a leftward swinging state. If the rotary switch 104 is pulled upwardly, the control box assembly 300 is unlocked. Then, the right rotary switch 104 is rotated clockwise to swing the snake-bone structure 500 rightwards. In this case, the rotary switch 104 is depressed downwardly to lock the control box assembly 300. At this time, the distal serpentine structure 500 of the surgical apparatus is maintained in the current state. Then, the surgical tool is inserted into the passageway of the upper connection sleeve 506 of the quick-change device 105 of the control box assembly 300, and the surgical tool presses the straight bar section of the unlocking bar 507 by friction, so that the groove in the surgical tool is engaged with the hook of the unlocking bar 507, such that the end effector of the surgical tool sequentially passes through the tool tube 114 of the control box, the front sheath assembly 101, the hose assembly 400 and the serpentine structure 500 of the surgical apparatus. The end effector of the surgical tool is arranged at the tip assembly 600 of the surgical apparatus with an operating handle end of the surgical tool being connected with the quick-change device 105 of the control box through the groove-hook engagement, so that the operating end of the surgical tool is positioned at the quick-change device 105 at the rear end of the control box and the end effector is disposed at the tip assembly 600 of the surgical apparatus, thereby fixing the surgical tool. Then, the triangle drive assembly 102 is adjusted by manually pulling the toggle rod 202 rearwards to linearly pull the transmission wire so as to drive the stretching wire 609 to be moved, thereby opening the triangular rings 102 on the tip assembly outwards, thus realizing movement output of the triangular ring 601 of the tip assembly 600 at the front end of the natural orifice surgical translumenal apparatus. In this case, a larger angle is formed between the two triangle rings 601 to change the position of the end effector of the surgical tool so that the end effector is as close as possible to the lesion tissue to form a better operating triangle region. The air-water switch 106 then is turned on for preparing to clean the organs. At this time, the surgical apparatus is ready, and the surgeon then can start minimally invasive surgery.

In order to overcome disadvantages in prior arts, an object of the disclosure is to provide a natural orifice translumenal minimally invasive surgical apparatus, which is small in volume, convenient to use, flexible in operation and has a large triangular region in surgical operation.

Finally, it should be noted that the above preferred embodiments are merely intended to illustrate the technical solutions of the disclosure, rather than limiting the scope thereof. The disclosure and embodiments thereof have been described above by way of illustration and the description is not restrictive. The accompanying drawings merely show some of embodiments of the disclosure, and the actual structure is not limited thereto. Therefore, those skilled in the art should understand that, without departing from the spirit of the disclosure, the equivalent changes and modifications made according to the scope of the disclosure, other transmission, drive devices and connection manners, and other structures and embodiments being similar to those in the technical solutions and designed without inventive steps, should all fall within the scope of the disclosure.

What is claimed is:

1. A natural orifice translumenal minimally invasive surgical apparatus, comprising a control box assembly, a hose assembly, a serpentine structure, and a tip assembly, wherein,
the control box assembly is sequentially and fixedly connected with the hose assembly, the serpentine structure and the tip assembly at a middle position of a distal end thereof;
the control box assembly comprises:
a control box housing having a rear wall provided with a quick-change device at either side thereof, the quick-change device including an upper connection sleeve into which a surgical tool is inserted; and
a triangular drive assembly including a knob cap operable to move the tip assembly at the distal end; and
wherein the hose assembly comprises an outer fixing sheath having a front end connected with an outer shell;
wherein the triangular drive assembly comprises a toggle lever passing through a middle portion of an upper housing of the control box assembly;
wherein the toggle lever is connected with the knob cap by a key at a top portion thereof, rotatably connected onto a holder by a connection pin at a rear end of a bottom portion thereof, and rotatably connected with a rear end of a pull rod by a connection pin at a front end of the bottom portion thereof, the pull rod being rotatably connected with a slider by a pin at a front end thereof;
wherein the slider is slidably connected with the holder by a guide rail and slider structure, the holder is fixed onto a partition plate of the control box assembly, a spring is fixed to a front end of the slider at a rear end thereof and is fixed on a front wall of the holder at a front end thereof, and the slider has a sliding axis coincident with an axis of a guide rail of the holder; and
wherein the apparatus further comprises a linear transmission wire having one end fixedly connected to one end of a triangular wire joint and the other end sequentially passing through a distal sheath assembly of the control box assembly, the hose assembly and the serpentine structure and then connected to a rear end of a transmission wire of the tip assembly.

2. The apparatus according to claim 1, wherein
the control box assembly further comprises two rotary switches;
each of the rotary switches comprises a swinging rod, at a top of which a swinging wheel is fixed, and a threaded bracket formed with a center hole in a top wall thereof and a cavity communicating with the center hole in a middle portion thereof;
the swinging rod has a lower portion passing through the center hole of the threaded bracket and extending into the cavity, and is engaged with the center hole of the threaded bracket through a clearance fit; and
an externally-toothed gear is fixed to a bottom portion of the swinging rod located in the threaded bracket, and an upper magnet assembly is fixed to a bottom wall of the externally-toothed gear.

3. The apparatus according to claim 2, wherein
the threaded bracket is fixed to a threaded seat, which is fixed onto a fixing plate by a fixing bolt;
an internally-geared ring is fixed in the threaded bracket;
a lower magnet assembly is fixed in an inner wall of a bottom portion of the threaded seat at a position opposite to the upper magnet assembly;
the externally-toothed gear is supported on a thrust spring;
the upper magnet assembly is wrapped within the thrust spring;
the thrust spring has an upper end in contact with a lower end of the externally-toothed gear in a non-stressed state thereof and a lower end fixedly connected with the lower magnet assembly;
a packing washer is sleeved over the thrust spring located at a lower portion of the internally-geared ring to radially fix the thrust spring;
axes of the internally-geared ring and the externally-toothed gear are coincident with an axis of the swinging rod, and the swinging rod is movable in an up-and-down direction to cause the internally-geared ring to engage with or disengage from the externally-toothed gear; and
sprockets are mounted on the swinging rod located at an upper part of the threaded bracket.

4. The apparatus according to claim 3, wherein
a set of chutes are fixed to the partition plate at a front side of each of the sprocket, respectively;
each set of chutes comprises two chutes disposed at a predetermined interval, and the sprocket on each swinging rod is engaged with a chain surrounding the sprocket;
each of the chains has two free ends disposed within the two chutes of one set of the chutes, respectively, and the chain is drivable by the swinging rod to reciprocate linearly in the chute; and
both of the free ends of each chain are connected with one end of four transmission wires, and the other end of each of the four transmission wires sequentially passes through the distal sheath assembly, a guide wire hole of a connection ring of the hose assembly and a guide wire hole of the serpentine structure and is then fixed in an rear end opening of a tip body of the tip assembly.

5. The apparatus according to claim 1, wherein
the two quick-change devices comprises two lower connection sleeves fixedly connected on the left and right sides of a rear wall of a lower housing of the control box housing, respectively;
each of the lower connection sleeves has a front end fixedly connected with a rear end of the tool tube at a corresponding side;
each of the lower connection sleeves is sleeved with and fixed to an outer telescopic sleeve having a center hole into which a middle telescopic sleeve is slidably inserted, and the middle telescopic sleeve has a center hole into which an inner telescopic sleeve is slidably inserted;
an upper connection sleeve is fixed to a rear end of the inner telescopic sleeve and is symmetrically formed with two rectangular slots of the same structure at either side along an axis thereof, and two unlocking bars of the same structure each comprise a straight bar segment inserted into the rectangular slot at a corresponding side through a clearance fit;
the straight bar segment has a rear end provided with a protruding hook hooked with a groove in the surgical tool and a front end connected with a pressing plate, and the bar segment of each unlocking bar is rotatably connected with the upper connection sleeve by a rotation shaft; and
the upper connection sleeve has a portion opposite to the pressing plate and fixedly connected with a push rod by a spring, wherein the pressing plate is allowed to be in contact with a top portion of the push rod when the unlocking bar is rotated about the rotation shaft.

6. The apparatus according to claim 1, wherein
the tip assembly comprises a tip body and an opening-closing body mounted in a middle groove of the tip body;
the opening-closing body includes two triangular rings having the same structure and symmetrically arranged in a left-and-right direction, and a triangular pulling rod is disposed at a middle position between the two triangular rings;
each of the triangular rings is symmetrically provided with a cylindrical boss and a cylindrical hole at either side thereof, wherein the cylindrical boss has an axis parallel to an axis of the cylindrical hole and perpendicular to an axis of the triangular ring, and each of the cylindrical bosses is rotatably connected with one end of each of links comprising two front links and two rear links, and the other ends of the two front links and the two rear links are respectively rotatably connected to front and the rear ends of the triangular pulling rod by pins;
a front end of a stretching wire is vertically and fixedly connected onto the triangular pulling rod, a triangular spring is sleeved over the stretching wire, and a rear end of the stretching wire passes through a middle opening of the tip body in which a boss is arranged;
the triangle spring is disposed in the middle opening with a predetermined gap therebetween and is fixedly connected to the boss at a lower end thereof, wherein in a state where axes of the two triangular rings are parallel with each other, an upper end of the triangular spring is in contact with a bottom end of the triangular pulling rod, and each cylindrical hole is rotatably connected with a cylindrical side of a triangular pin fixed onto the tip body, so that the triangular ring is rotatable about the triangular pin; and
the tip body is provided with arc grooves in a middle slotted inner wall thereof corresponding to the four cylindrical bosses, and an end portion of each cylindrical boss of the triangular rings is slidably disposed in a corresponding one of the arc grooves, the cylindrical boss is slidable back and forth in the arc groove, and the triangular pulling rod, the links, the triangular pin and the triangular ring are rotatably connected together to form a four-link mechanism.

7. The apparatus according to claim 1, further comprising a water-air switch connected onto the upper housing.

* * * * *